US00PP13852P39

(12) United States Plant Patent
van Heesbeen

(10) Patent No.: US PP13,852 P3
(45) Date of Patent: May 27, 2003

(54) EUONYMUS PLANT NAMED 'HEESPIERROLINO'

(75) Inventor: Andianus L. P. van Heesbeen, Haarsteeg (NL)

(73) Assignee: Van Heesbenn Cultures BV, Haarsteeg (NL)

( * ) Notice: Subject to any disclaimer, the term of this patent is extended or adjusted under 35 U.S.C. 154(b) by 102 days.

(21) Appl. No.: 09/838,276

(22) Filed: Apr. 20, 2001

(65) Prior Publication Data

US 2001/0047528 P1 Nov. 29, 2001

(30) Foreign Application Priority Data

Apr. 20, 2000 (EP) ..... 2000/0663

(51) Int. Cl.[7] ..... A01H 5/00
(52) U.S. Cl. ..... Plt./246; Plt./226
(58) Field of Search ..... Plt./246, 226

(56) References Cited

PUBLICATIONS

UPOV ROM GTITM Computer Database, GTI JOUVE retrieval software 2002/02 citation(s) for 'Heespierrolino' and Hees01.*

* cited by examiner

*Primary Examiner*—Bruce R. Campell
*Assistant Examiner*—W C Haas
(74) *Attorney, Agent, or Firm*—Foley & Lardner

(57) ABSTRACT

A new and distinct *Euonymus japonicus* plant named 'Heespierrolino' characterized by having green, variegated, and white leaves, stems, and branches; white young leaves and sprigs; year round white sprig production; a broad and erect growth habit of up to 30 cm long; a good winter hardiness; and no flowers. 'Heespierrolino' is an evergreen, has been found stable and is reproduced by cuttings. Branches of 'Heespierrolino' remain white for a long period and eventually turn green from the base but the youngest part as well as youngest leaves remain white.

2 Drawing Sheets

LATIN NAME OF THE GENUS AND SPECIES OF THE PLANT CLAIMED

*Euonymus japonicus.*

VARIETY DENOMINATION

Heespierrolino; c.v. Pierrolino.

BACKGROUND OF THE INVENTION

The present invention relates to a new and distinct cultivar of Euonymus plant, hereinafter referred to by the cultivar name 'Heespierrolino'. 'Heespierrolino' is a spontaneous mutant of an unnamed *Euonymus japonicus* cultivar selected by or under the supervision of the inventor, Adrianus L. P. van Heesbeen, in a cultivated environment in Haarsteeg, The Netherlands.

Asexual reproduction of the new cultivar by stem cutting was first performed at the end of 1997 in Haarsteeg, The Netherlands and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Heespierrolino' which in combination distinguish this *Euonymus japonicus* as a new and distinct cultivar:

1. White coloration of young leaves and young sprigs;
2. Broad and erect growth habit; and
3. White sprig production year round when pinched.

'Heespierrolino' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Haarsteeg, The Netherlands, under conditions which closely approximate those generally used in commercial practice.

Of the many commercial cultivars known to the present inventor, the most similar in comparison to 'Hees01' is cultivar *Euonymus fortunei* 'Harlequin'. 'Heespierrolino' produces young sprigs almost year round. 'Harlequin' produces white sprigs only in April, May, June, and July. 'Heespierrolino' grows more erect and less broad than 'Harlequin' while the rate of growth of 'Harlequin' is slightly slower. The young leaves of 'Heespierrolino' are whiter and much less speckled than the young leaves of 'Harlequin'.

'Heespierrolino' produces more, though shorter branches than 'Harlequin'. The branches of 'Heespierrolino' stay white for a long time, sometimes up to the roots with small green stripes along the length stripes in the middle to the bottom. The branches of 'Harlequin' are green with green/white stripes are more green/white than white although vertically they still have green stripes.

The leaf shape of 'Heespierrolino' is obovate to elliptic whereas 'Harlequin' has ovate shaped leaves. Leaf base of 'Heespierrolino' is acute, the leaf base of 'Harlequin' is obtuse. The leaf length of 'Heespierrolino' is up to 5 cm, and width up to 2.5 cm, while the leaf length of 'Harlequin' is up to 3 cm and width up to 2 cm. The petiole length of 'Heespierrolino' at 5–7 mm is longer than the petiole length of 'Harlequin' at 3–5 mm.

BRIEF DESCRIPTION OF THE DRAWING

The accompanying photographic illustrations show a plant of Euonymus 'Heespierrolino', with colors being as true as possible with illustrations of this type.

The first drawing shows a full view of 'Heespierrolino'.

The second drawing shows a comparison between 'Heespierrolino' and 'Harlequin'.

DETAILED BOTANICAL DESCRIPTION

The following observations, measurements and values describe the new cultivar as grown in Haarsteeg, The Netherlands, under conditions which closely approximate those generally used in commercial practice. The plants are grown in a normal glasshouse. Average day and night floor temperatures are 18 degrees Celsius. At this temperature, it takes 1 month for a cutting to initiate roots (throughout the year), and 3 months to produce a rooted cutting or liner. Roots are freely branching and rate of growth is approximately 15 cm a year. Fertilizes (no special kind) are added regularly. The plants need a normal amount of water and need to be grown in fluffy soil. As with most Euonymous varieties, 'Heespierrolino' should not be kept in soil that is very wet for too long.

Overall garden performance and weather tolerance is excellent. 'Heespierrolino' has been grown from temperatures of minus 15 degrees Celsius to 45 degrees Celsius. No damage or any symptoms of stress were observed. Resistance, tolerance or susceptibility to stresses, pathogens, and pests is good. Pesticides are used against lice and spider mites. Color references are made to The Royal Horticultural Society Colour Chart (R.H.S.), except where general colors of ordinary significance are used. Color values were taken under daylight conditions at approximately noon in Rijswijk, The Netherlands.

Of the *Euonymous japonicus* plants in the breeder's nursery in The Netherlands, a mutant was selected in 1997, primarily for its color, and designated 'Heespierrolino'. Its potential was further evaluated when propagated by vegetative cuttings. In the following years, this variety was further evaluated on its characteristics and stability. Four generations have been propagated since.

Propagation: Stem cutting.

Plant:

*Form.*—Upright, bushy.

*Growth habit.*—Two year old plant: Broad and erect, 25 cm high and 15 cm wide. Mature plant: Broad and erect, 25–30 cm in The Netherlands.

*Winter hardiness.*—Plants have been grown in temperatures as low as minus 15 degrees Celsius without observing any damage or other changes.

*Stems.*—Texture: Glabrous, no pubescence. Color: Base is green RHS 145C, or 146B or a combination of both and sometimes combined with white RHS 155C and/or brown RHS 166B. Going upwards, the stem gets more and more white lines and is eventually pure white. Branches of 'Heespierrolino' stay white for a long time, sometimes up to the node with small green stripes along the length stripes in the middle to the bottom (similar to the main stem).

*Internodes.*—Length up to 30 mm.

*Roots.*—Freely branching, growth rate approximately 15 cm a year.

Foliage:

*Type.*—Single, opposite, and symmetrical arrangement, no pubescence.

*Shape.*—Obovate to elliptic, tip is acute, base is acute.

*Color.*—Center color of leaf: Green RHS 139A, or variegated, or white RHS 155D. Upper side: Mature leaf is dark green RHS 139A with light green to white spots; young leaf is white RHS 155D. Underside: Mature leaf is green RHS 137C, with gray/green spots RHS 190C; young leaf is white RHS 155D. Edges of leaf: Green, white, or variegated (same colors as underside).

*Size of leaf.*—Up to 5 cm. Width: Up to 2.5 cm. Length: Up to 5 cm.

*Petioles.*—Length is up to 5–7 mm; diameter is up to 1 mm; mature leaf petiole is green RHS 139C but may have white/green on underside; young leaf petiole color is white RHS 155D.

*Orientation.*—Opposite.

*Leaf texture.*—Smooth, glossy and leathery.

*Veining.*—Pinnate.

*Leaf margins.*—Crenate, serrate.

OTHER OBSERVATIONS

Flowers: 'Heespierrolino' is a non-flowering evergreen.

Winter hardiness: 'Heespierrolino' has been grown from temperatures of minus 15 degrees Celsius to 45 degrees Celsius with no damage or symptoms of stress observed.

Disease/pest resistance/susceptibility: Resistance, tolerance, and/or susceptibility to stresses, pathogens, and pests is good.

I claim:

1. A new and distinct Euonymus plant named 'Heespierrolino', substantially as illustrated and described herein.

* * * * *

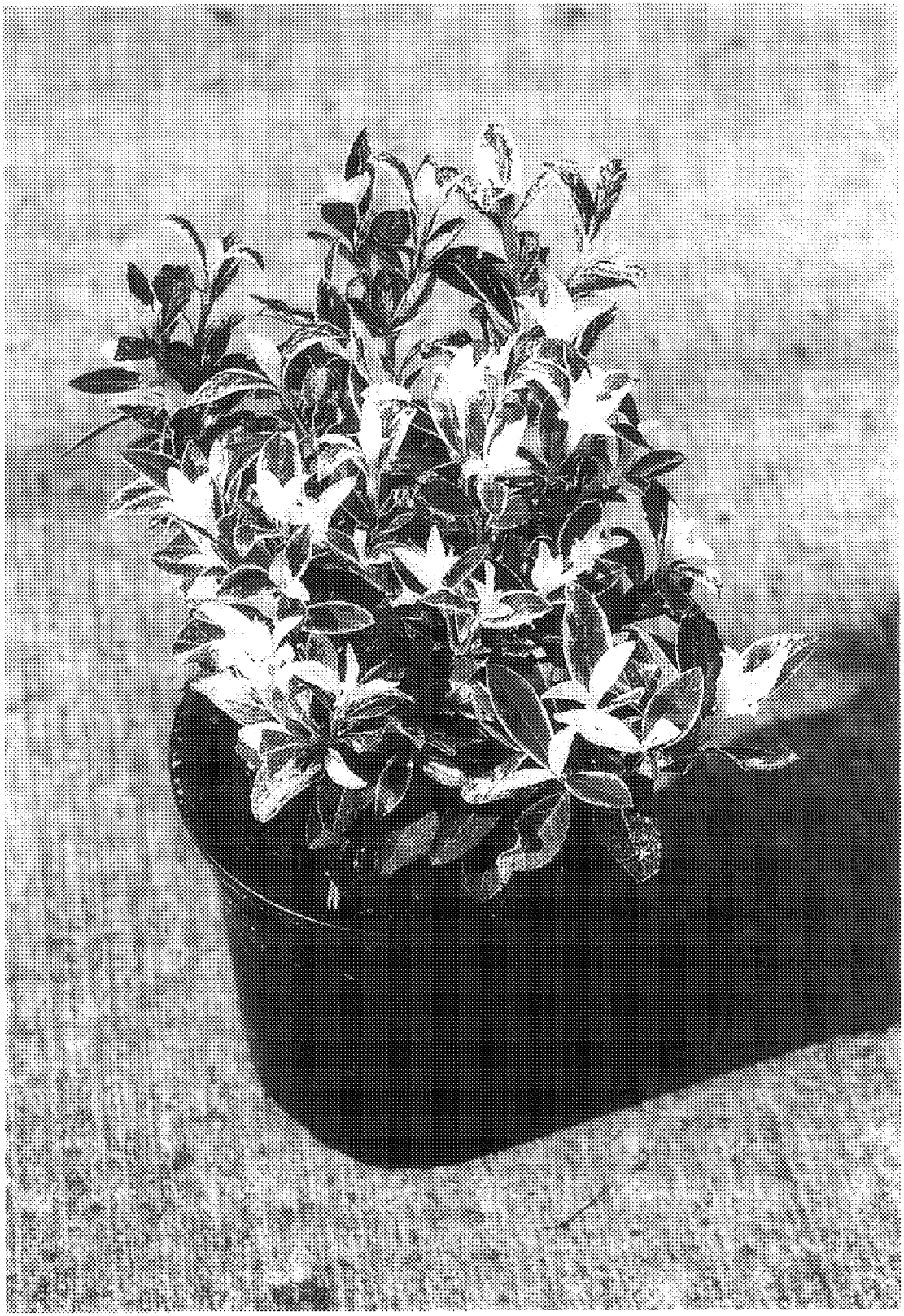

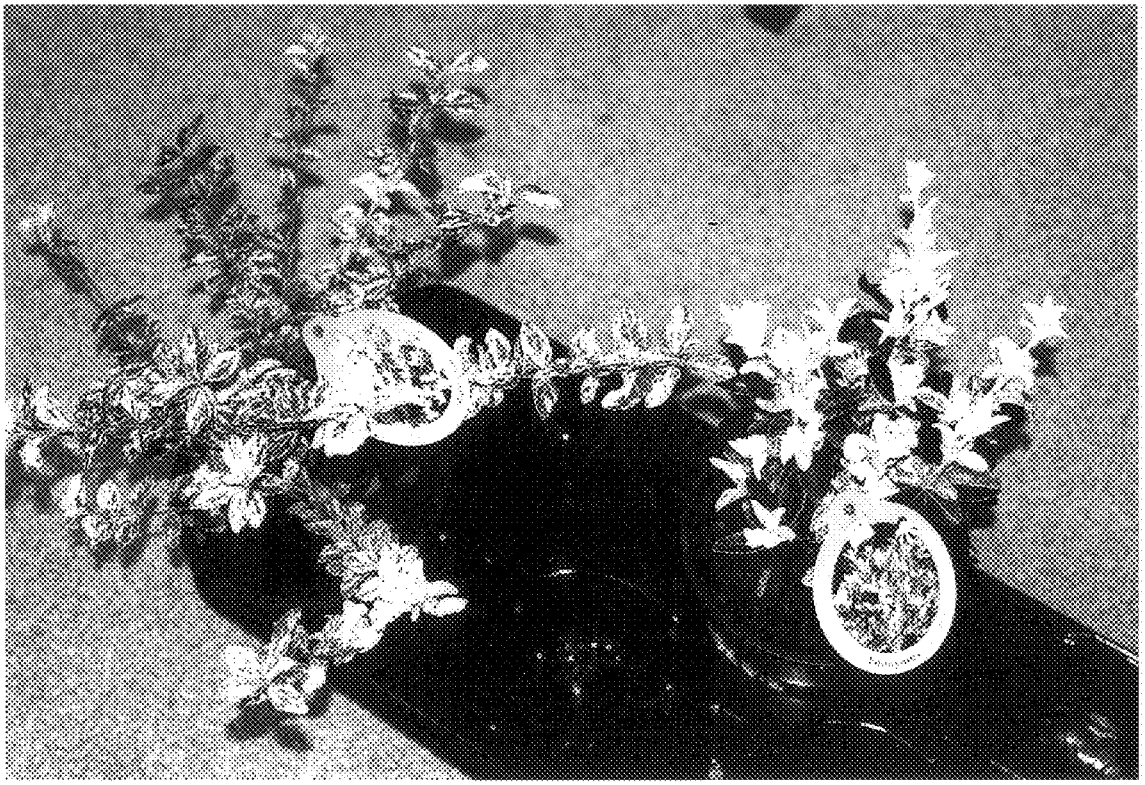

UNITED STATES PATENT AND TRADEMARK OFFICE

CERTIFICATE OF CORRECTION

PATENT NO. : PP 13,852 P3
DATED : May 27, 2003
INVENTOR(S) : Adrianus L.P. Van Heesbeen It is certified that error appears in the above-identified patent and that said Letters Patent is hereby corrected as shown below:

Title page,
Item [75], please correct the name of the Inventor to read:
-- Adrianus L.P. van Heesbeen --

Signed and Sealed this

Fourth Day of November, 2003

JAMES E. ROGAN
*Director of the United States Patent and Trademark Office*